(12) United States Patent
Brooks

(10) Patent No.: US 11,491,041 B2
(45) Date of Patent: Nov. 8, 2022

(54) PERI-PELVIC POST-OPERATIVE SUPPORT ASSEMBLY

(71) Applicant: Catherine Brooks, Solana Beach, CA (US)

(72) Inventor: Catherine Brooks, Solana Beach, CA (US)

(*) Notice: Subject to any disclaimer, the term of this patent is extended or adjusted under 35 U.S.C. 154(b) by 0 days.

(21) Appl. No.: 17/720,780

(22) Filed: Apr. 14, 2022

(65) Prior Publication Data

US 2022/0296405 A1 Sep. 22, 2022

Related U.S. Application Data

(63) Continuation-in-part of application No. 17/495,577, filed on Oct. 6, 2021, now Pat. No. 11,304,455.

(60) Provisional application No. 63/164,485, filed on Mar. 22, 2021.

(51) Int. Cl.
| | |
|---|---|
| *A61F 5/03* | (2006.01) |
| *A61F 13/14* | (2006.01) |
| *A61F 5/02* | (2006.01) |
| *A61F 13/00* | (2006.01) |
| *A41C 1/08* | (2006.01) |

(52) U.S. Cl.
CPC ............... *A61F 5/03* (2013.01); *A61F 5/02* (2013.01); *A61F 13/148* (2013.01); *A41C 1/08* (2013.01); *A61F 2013/00493* (2013.01)

(58) Field of Classification Search
CPC .. A61F 5/02; A61F 5/03; A61F 13/148; A61F 2013/00493; A41C 1/08; A41C 1/10
See application file for complete search history.

(56) References Cited

U.S. PATENT DOCUMENTS

| | | | |
|---|---|---|---|
| 4,557,268 A | 12/1985 | Maddux et al. | |
| 4,697,592 A | 10/1987 | Maddux et al. | |
| 4,759,083 A | 7/1988 | Belcher | |
| 4,789,372 A | 12/1988 | Wicks | |
| 4,802,469 A | 2/1989 | Gollestani | |
| 4,867,145 A | 9/1989 | Goth | |
| 5,094,648 A | 3/1992 | Turner | |
| 5,217,403 A * | 6/1993 | Nobbs | A41C 1/10 2/237 |
| 5,403,271 A | 4/1995 | Saunders et al. | |
| 5,528,775 A | 6/1996 | Marenda | |
| 5,613,893 A | 3/1997 | Zagame | |
| 5,743,783 A | 4/1998 | Weber-Unger | |
| 5,765,224 A | 6/1998 | Johnson | |

(Continued)

*Primary Examiner* — Keri J Nelson
(74) *Attorney, Agent, or Firm* — Roeder & Broder LLP; James P. Broder

(57) ABSTRACT

A support assembly (100) for supporting a transverse incision site (420) of a user (101) includes an assembly body (106) and a first assembly arm (102). The assembly body (106) is configured to encircle an abdomen (107) and at least one leg (311) of the user (101). The assembly body (106) includes a pelvic support layer (214) that is configured to provide a transverse supportive force to the transverse incision site (420) of the user (101). The first assembly arm (102) is coupled to the pelvic support layer (214). The first assembly arm (102) extends anteriorly from the assembly body (106). The first assembly arm (102) is configured to extend from a groin region (109) of the user (101) and secure to the assembly body (106) to adjust the transverse supportive force to the transverse incision site (420) at the peripelvic area (421).

20 Claims, 9 Drawing Sheets

(56) References Cited

U.S. PATENT DOCUMENTS

| | | |
|---|---|---|
| 5,928,059 A | 7/1999 | Wicks |
| 6,063,049 A | 5/2000 | Watkins |
| 6,080,125 A | 6/2000 | Mott |
| 6,085,750 A | 7/2000 | Majkutewicz |
| 6,112,704 A | 9/2000 | Altafi |
| 6,146,240 A | 11/2000 | Morris |
| 6,270,469 B1 | 8/2001 | Mott |
| 6,620,026 B1 | 9/2003 | Guilani et al. |
| 6,629,942 B1 | 10/2003 | Tubbs |
| 6,846,220 B2 | 1/2005 | Wakefield |
| 7,425,171 B2 | 9/2008 | Maupin |
| 7,441,418 B2 | 10/2008 | Delgado-Mecinas |
| 7,556,610 B2 | 7/2009 | Binder et al. |
| 7,934,507 B2 | 5/2011 | Brooks |
| 7,938,121 B2 | 5/2011 | McKnight et al. |
| 7,999,146 B2 | 8/2011 | Brothers |
| 8,414,352 B2 | 4/2013 | Trenhaile |
| 8,430,830 B1 | 4/2013 | Ariza |
| 8,506,509 B1 | 8/2013 | Ariza |
| 8,615,815 B2 | 12/2013 | Dahlquist |
| 8,707,464 B2 | 4/2014 | Trenhaile |
| 8,752,216 B2 | 6/2014 | Sawle et al. |
| 8,764,691 B2 | 7/2014 | Sharps et al. |
| 8,784,351 B2 | 7/2014 | Dumpson et al. |
| 8,881,732 B2 | 11/2014 | Blurton et al. |
| 8,945,030 B2 | 2/2015 | Weston |
| 9,161,574 B2 | 10/2015 | Swendseid et al. |
| 9,161,854 B2 | 10/2015 | Fruscione-Loizides |
| 9,220,627 B2 | 12/2015 | Fisher |
| 9,398,972 B2 | 7/2016 | Yip et al. |
| 9,452,100 B2 | 9/2016 | Bigelow |
| 9,585,983 B1 | 3/2017 | Brahm |
| 9,687,395 B2 | 6/2017 | Clarke |
| 9,737,455 B2 | 8/2017 | Argenta et al. |
| 9,795,500 B2 | 10/2017 | Ingimundarson et al. |
| 9,867,400 B2 | 1/2018 | Solano et al. |
| 9,867,402 B2 | 1/2018 | West et al. |
| D826,516 S | 8/2018 | Vopni et al. |
| 10,085,770 B2 | 10/2018 | Blurton et al. |
| 11,147,705 B2 * | 10/2021 | Sarna .................. A41C 1/08 |
| 2007/0077860 A1 | 4/2007 | Brooks |
| 2008/0254712 A1 | 10/2008 | Christensen |
| 2009/0138034 A1 | 5/2009 | Maliglowka |

\* cited by examiner

PERI-PELVIC POST-OPERATIVE SUPPORT ASSEMBLY

RELATED APPLICATION

The present application is a continuation-in-part application claiming the benefit under 35 U.S.C. 120 on co-pending U.S. patent application Ser. No. 17/495,577, filed on Oct. 6, 2021, and entitled "PERI-PELVIC POST-OPERATIVE SUPPORT ASSEMBLY," which claims priority on U.S. Provisional Application Ser. No. 63/164,485, filed on Mar. 22, 2021, and entitled "PERI-PELVIC POST-OPERATIVE SUPPORT ASSEMBLY." As far as permitted, the contents of U.S. patent application Ser. No. 17/495,577 and U.S. Provisional Application Ser. No. 63/164,485 are incorporated herein by reference.

BACKGROUND

Cesarean section (C-section) delivery is one of the most common surgeries in the United States. Each year, approximately 1.3 million women deliver by C-section and experience the subsequent risks and abdominal surgery recovery. A Pfannenstiel or low transverse abdominal incision occurs at the "bikini line," and significant amounts of tissue handling also occur at the abdominal area resulting in a two-fold problem to address. Edema, fluid, and gas collection occur in the trunk and at the incision, while the incision has the added factor of being a healing wound. Compounding the problem is that gravity causes fluids from swelling to flow downward, pooling into the pelvic area resulting in increased pressure on the interior incision, thereby creating a risk for wound complications.

For the Cesarean and low Pfannenstiel incisions, edema is also combined with the internal pressure change of coughing, laughing, and/or transitioning to stand, sit or lie down, contributing to wound stress and other complications. Rates for these Cesarean healing complications, depending on inclusion criteria, can range from 5.2% to 12.5%.

Binders are often used post-cesarean to address abdominal discomfort post-operation. Unfortunately, binders are designed to address the abdomen and low back alone, ignoring the need for wound support and peri-incisional edema control. This type of abdominal support can pose risks at the transverse incision site with this downward pressure. While supporting the abdomen, binders can leave the bikini line incision unchecked, but they can promote a situation where compression is superior to the incision, causing gas and fluids to flow inferiorly into the incision area. When binders are pulled down to address the incision area, they can also impact the hip joint, impeding sitting and walking. The binders can adversely affect don/doff mobility and provide inconsistent incision support at best.

Wound visualization, cleaning, and examination by clinical staff and the patient is routine during surgical recovery and another priority post-operative need. The incision complication rate equals approximately 65,000 to 162,000 wound complications annually when viewed in light of the complication rate data (5-12.5%) and Cesarean statistics (1.3 million). However, these approximations do not consider other surgical procedures. Other surgical procedures can include hysterectomies and other gynecologic or pelvic procedures. Wound visualization of the entire field is paramount for the care of these patients and those that are healing without complications for routine wound care and check.

SUMMARY

The present invention is directed toward a support assembly for supporting a transverse incision site at a peri-pelvic area of a user, the user having an abdomen, at least one leg, and a groin region. In various embodiments, the support assembly includes an assembly body and a first assembly arm. The assembly body is configured to encircle (i) the abdomen of the user, and (ii) the at least one leg of the user. The assembly body includes a pelvic support layer that is configured to provide a transverse supportive force to the transverse incision site of the user. The first assembly arm is coupled to the pelvic support layer. The first assembly arm extends anteriorly from the assembly body. The first assembly arm is configured to extend from the groin region of the user and secure to the assembly body to adjust the transverse supportive force to the transverse incision site at the peri-pelvic area.

In some embodiments, the support assembly further includes a second assembly arm that is secured to the assembly body, wherein the first assembly arm has a first arm end that is detachably fastenable to one of (i) the second assembly arm, and (ii) the assembly body.

In various embodiments, the first arm end includes a first arm fastener that detachably fastens the first assembly arm to one of (i) the second assembly arm, and (ii) the assembly body.

In certain embodiments, the assembly body includes a groin portion configured to cover a groin region of the user, the groin portion being positioned adjacent to the pelvic support layer.

In some embodiments, the assembly body includes an edge band that encircles and is configured to conform to a portion of the abdomen of the user, the edge band being at least partially formed from an elastic material.

In various embodiments, the support assembly further includes a second assembly arm that is secured to the assembly body, the assembly body including a second arm securer, wherein the second assembly arm is coupled to a second arm securer of the assembly body.

In certain embodiments, the support assembly further includes a second assembly arm that is secured to the assembly body, wherein the support assembly is movable between (i) a dressed configuration wherein the assembly body encircles the user and the second assembly arm is fastened to the first assembly arm, (ii) a partially dressed configuration wherein the assembly body encircles the user and the second assembly arm is detached from the first assembly arm, and (iii) an undressed configuration wherein the assembly body is decoupled from the user and the second assembly arm is detached from the first assembly arm.

In some embodiments, in the dressed configuration, the pelvic support layer is positioned in between the first assembly arm and an incision support layer.

In various embodiments, in the dressed configuration, the first assembly arm is fastened to the second assembly arm at a plurality of fastening points.

In certain embodiments, the support assembly is movable between the dressed configuration and the partially dressed configuration without removing the assembly body from the abdomen of the user.

In some embodiments, in the undressed configuration, the first assembly arm, the second assembly arm, and the pelvic support layer are substantially parallel to one another.

The present invention is directed toward a support assembly for supporting a transverse incision site at a peri-pelvic area of a user, the user having an abdomen, at least one leg, and a groin region. In various embodiments, the support assembly includes an assembly body and a first assembly arm. The assembly body is configured to encircle (i) the abdomen of the user, and (ii) the at least one leg of the user. The assembly body includes a pelvic support layer that is configured to provide a transverse supportive force to the transverse incision site of the user. The first assembly arm is coupled to the pelvic support layer. The first assembly arm extends anteriorly from the assembly body. The first assembly arm is configured to extend from the groin region of the user and secure to the assembly body to adjust the transverse supportive force to the transverse incision site at the peri-pelvic area. The support assembly is movable between (i) a dressed configuration wherein the assembly body encircles the user, and the first assembly arm is fastened to the first assembly arm, (ii) a partially dressed configuration wherein the assembly body encircles the user, and the first assembly arm is detached from the first assembly arm, and (iii) an undressed configuration wherein the assembly body is decoupled from the user, and the first assembly arm is detached from the first assembly arm.

In various embodiments, the assembly body includes a groin portion that is configured to cover the groin region of the user, the groin portion being positioned adjacent to the pelvic support layer.

In certain embodiments, the assembly body includes an edge band that encircles and is configured to conform to a portion of the abdomen of the user, the edge band being at least partially formed from an elastic material.

In some embodiments, in the dressed configuration, the pelvic support layer is positioned in between the first assembly arm and an incision support layer.

In various embodiments, in the undressed configuration, at least a portion of the assembly body has a somewhat hourglass-shaped configuration.

In certain embodiments, the support assembly further includes a second assembly arm that is coupled to a second arm securer of the assembly body, the second assembly arm being detachably fastenable to the first assembly arm, the second arm securer being coupled to the assembly body.

In some embodiments, the first arm end includes a first arm fastener that detachably fastens the first assembly arm to at least one of the assembly body and the first assembly arm.

The present invention is directed toward a support assembly for supporting a transverse incision site at a peri-pelvic area of a user, the user having an abdomen, at least one leg, and a groin region. In various embodiments, the support assembly includes an assembly body, a first assembly arm, and a second assembly arm. The assembly body is configured to encircle (i) the abdomen of the user, and (ii) the at least one leg of the user. The assembly body includes a pelvic support layer that is configured to provide a transverse supportive force to the transverse incision site of the user. The first assembly arm is coupled to the pelvic support layer. The first assembly arm extends anteriorly from the assembly body. The first assembly arm is configured to extend from the groin region of the user and secure to the assembly body to adjust the transverse supportive force to the transverse incision site at the peri-pelvic area. The second assembly arm is secured to the assembly body. The assembly body includes a second arm securer. The second assembly arm is coupled to a second arm securer of the assembly body. The support assembly is movable between (i) a dressed configuration wherein the assembly body encircles the user and the second assembly arm is fastened to the first assembly arm, and the pelvic support layer is positioned in between the first assembly arm and an incision support layer, (ii) a partially dressed configuration wherein the assembly body encircles the user and the second assembly arm is detached from the first assembly arm, and (iii) an undressed configuration wherein the assembly body is decoupled from the user and the second assembly arm is detached from the first assembly arm, in the dressed configuration.

This summary is an overview of some of the teachings of the present invention and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
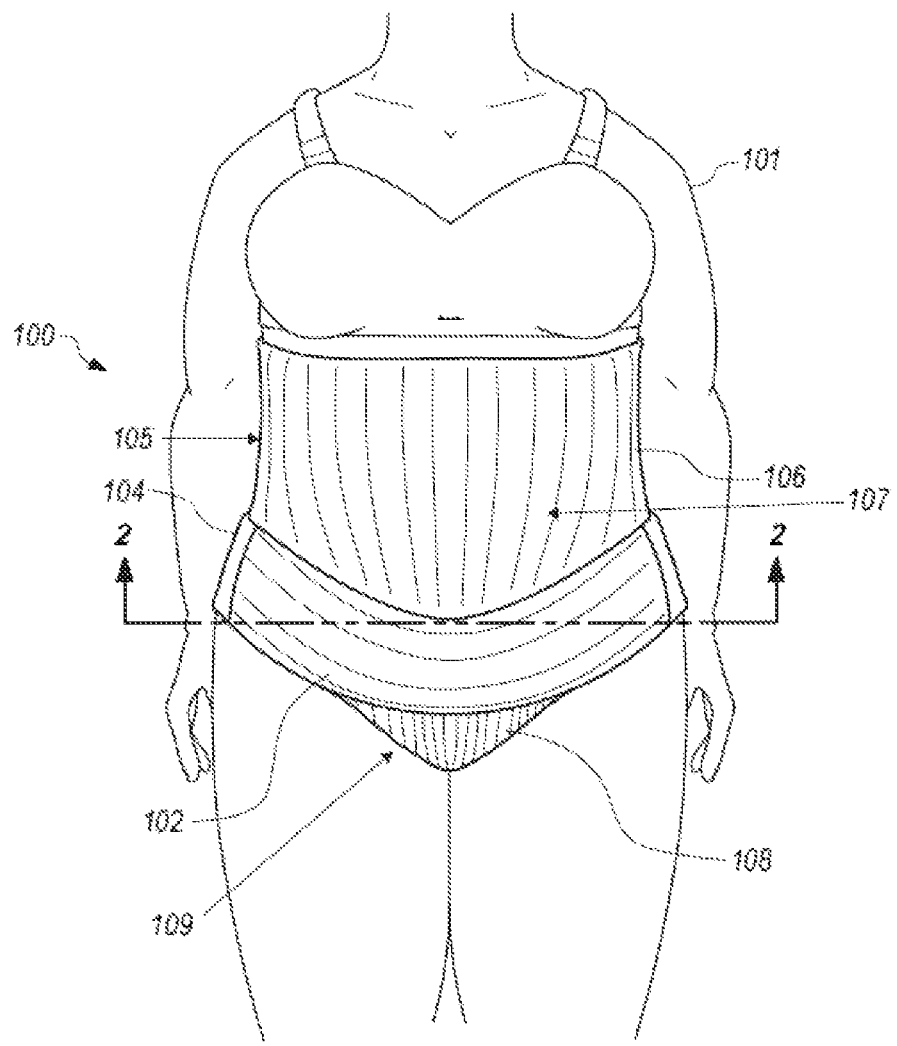
FIG. 1 is a front view of a user and an embodiment of a peri-pelvic post-operative support assembly shown in a dressed configuration, the support assembly having features of the present invention.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Embodiments of the present invention are described herein in the context of a peri-pelvic post-operative support assembly that is configured to meet the compound, transverse incision care requirements of a user. In particular, the present technology can be used to meet the post-operative wound care needs of a low-transverse abdominal (e.g., the Pfannenstiel) incision site (sometimes referred to herein as the "transverse incision site"). However, the peri-pelvic post-operative support assembly can be configured to support any wound. The wound care needs include prioritized incision support, lesser graded abdominal support, and a mechanism for wound visualization integrated into the support assembly. The support assembly can include one or more features configured to meet the unique and concurrent needs for the most common incision into a woman's body at the anterior uterus or "bikini line." The present technology can address the complex recovery from uterine and peri-abdominal surgery, most often noted after a cesarean section or a hysterectomy. The present technology can also be utilized for hernia repair and/or other abdominal and gynecologic surgeries. The present technology can further be utilized for other gynecologic procedures or may be applied to gender-neutral hernia repair or other abdominal, orthopedic, vascular exposures that require peri-pelvic lower quadrant surgical exposure or gender-neutral procedures that require peri-pelvic lower quadrant surgical exposure.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention, as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming. However, it would nevertheless be a routine undertaking of engineering for those of ordinary skill in the art having the benefit of this disclosure.

Figure 2:
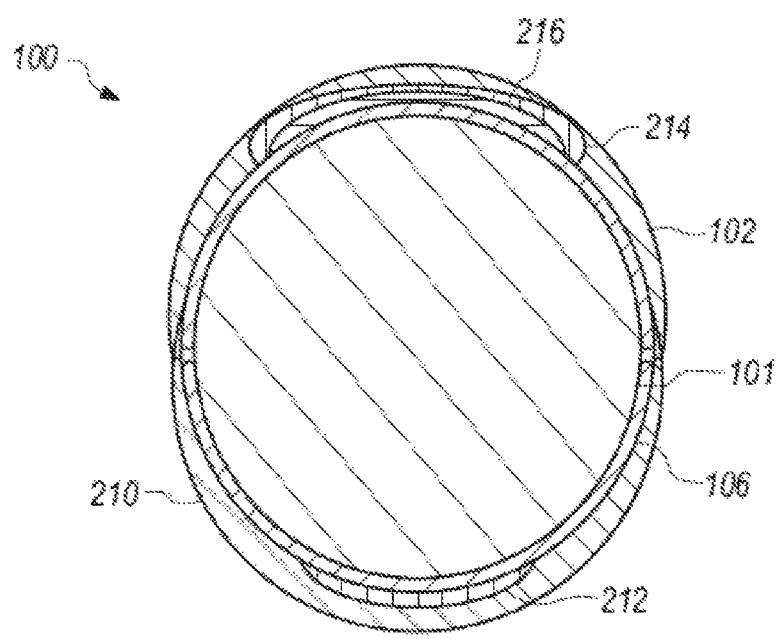
FIG. 2 is a simplified cross-sectional view of the user and an embodiment of the support assembly taken on line 2-2 in FIG. 1.

FIG. 1 is a front view of a user 101 and an embodiment of a peri-pelvic post-operative support assembly 100 in accordance with various embodiments herein. In FIG. 1, the support assembly 100 is shown in a dressed configuration. As used herein, the "dressed configuration" is understood to mean when an assembly body 106 encircles the user 101 and at least one of a first assembly arm 102 and a second assembly arm 210 (illustrated in FIG. 2) is fastened to the first assembly arm 102. Two non-limiting, non-exclusive examples of the dressed configuration of the support assembly 100 are shown in FIGS. 1-2. While the user 101 shown and described herein is female, it is appreciated that the support assembly 100 can be configured or modified for any suitable gender (e.g., one or more embodiments of the support assembly 100 can be gender-neutral) in accordance with the goals of the technology disclosed herein.

Figure 3:
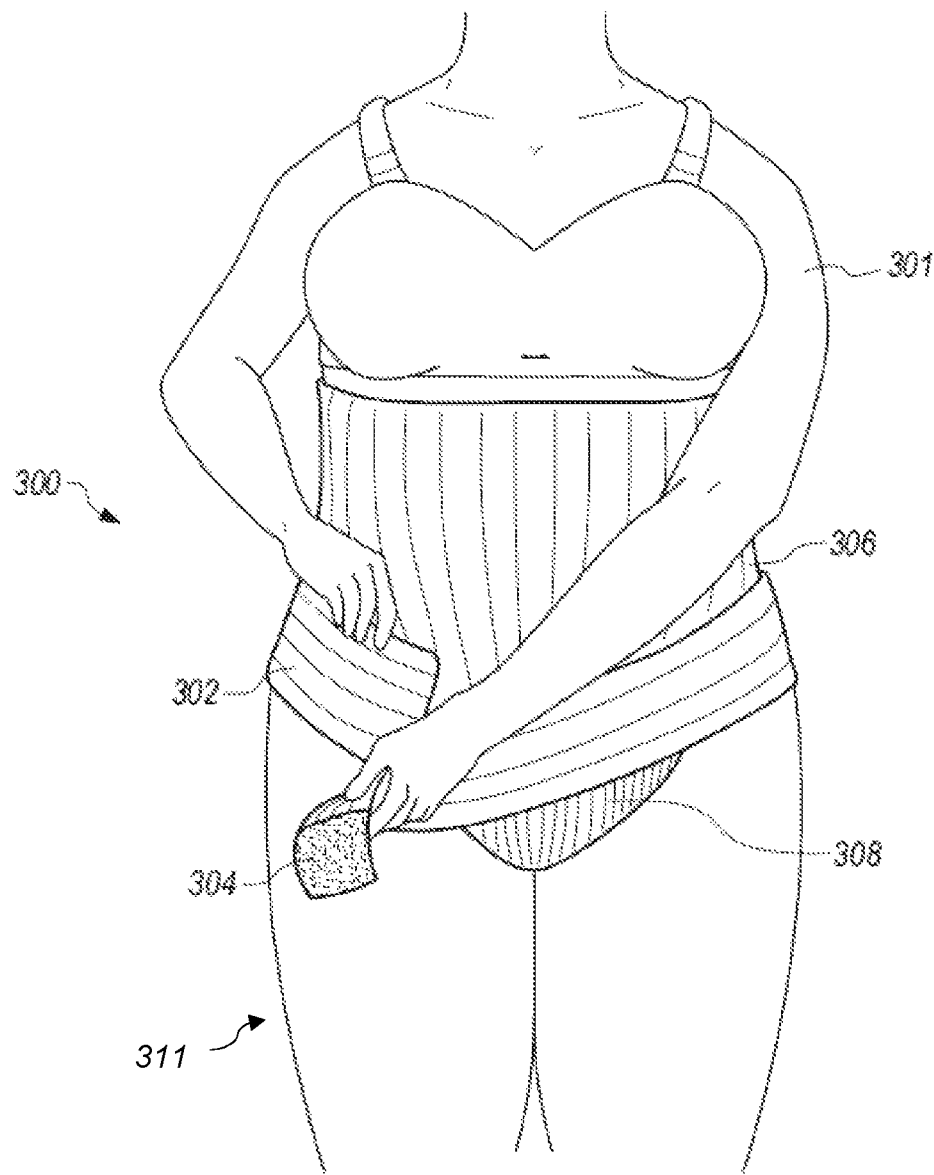
FIG. 3 is a front view of the user and an embodiment of the support assembly shown in a partially dressed configuration.
Figure 4:
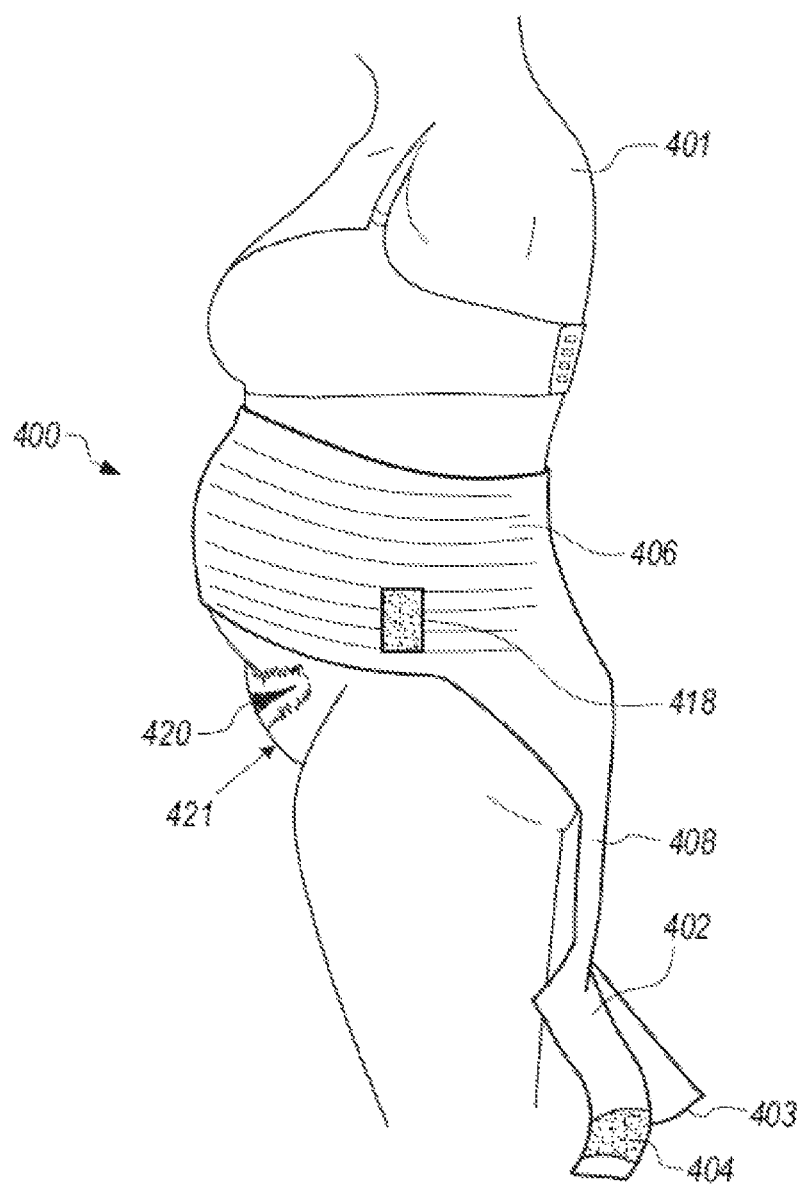
FIG. 4 is a left side view of the user and an embodiment of the support assembly shown in the partially dressed configuration.
Figure 5:
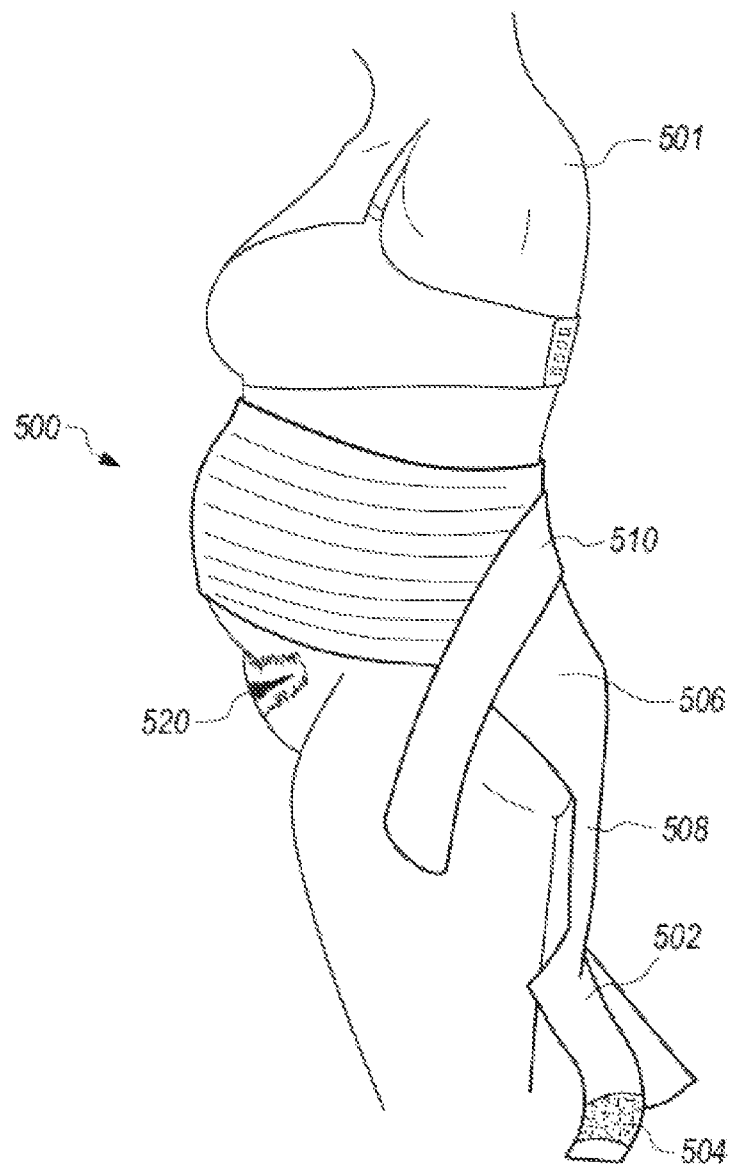
FIG. 5 is a left side view of the user and yet another embodiment of support assembly shown in the partially dressed configuration.

As used herein, the "partially dressed configuration" is understood to mean when the assembly body 106 encircles the user 101 and at least one of the first assembly arm 102 and the second assembly arm 210 is detached from the first assembly arm 102. FIGS. 3-5 demonstrate non-limiting, non-exclusive examples of when the support assembly 100 is in the partially dressed configuration.

Figure 6:
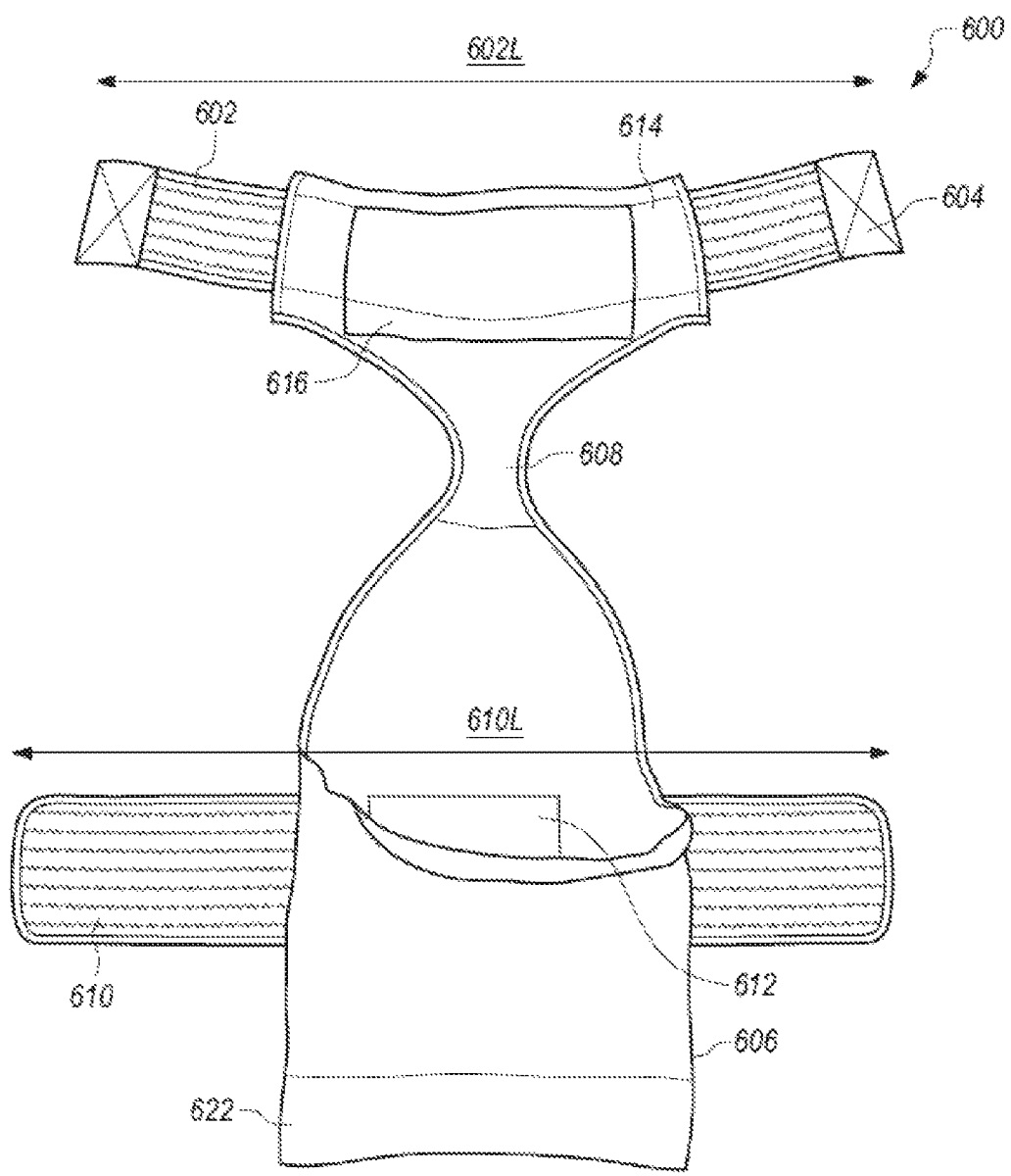
FIG. 6 is a top view of an embodiment of the support assembly shown in an undressed configuration.
Figure 7:
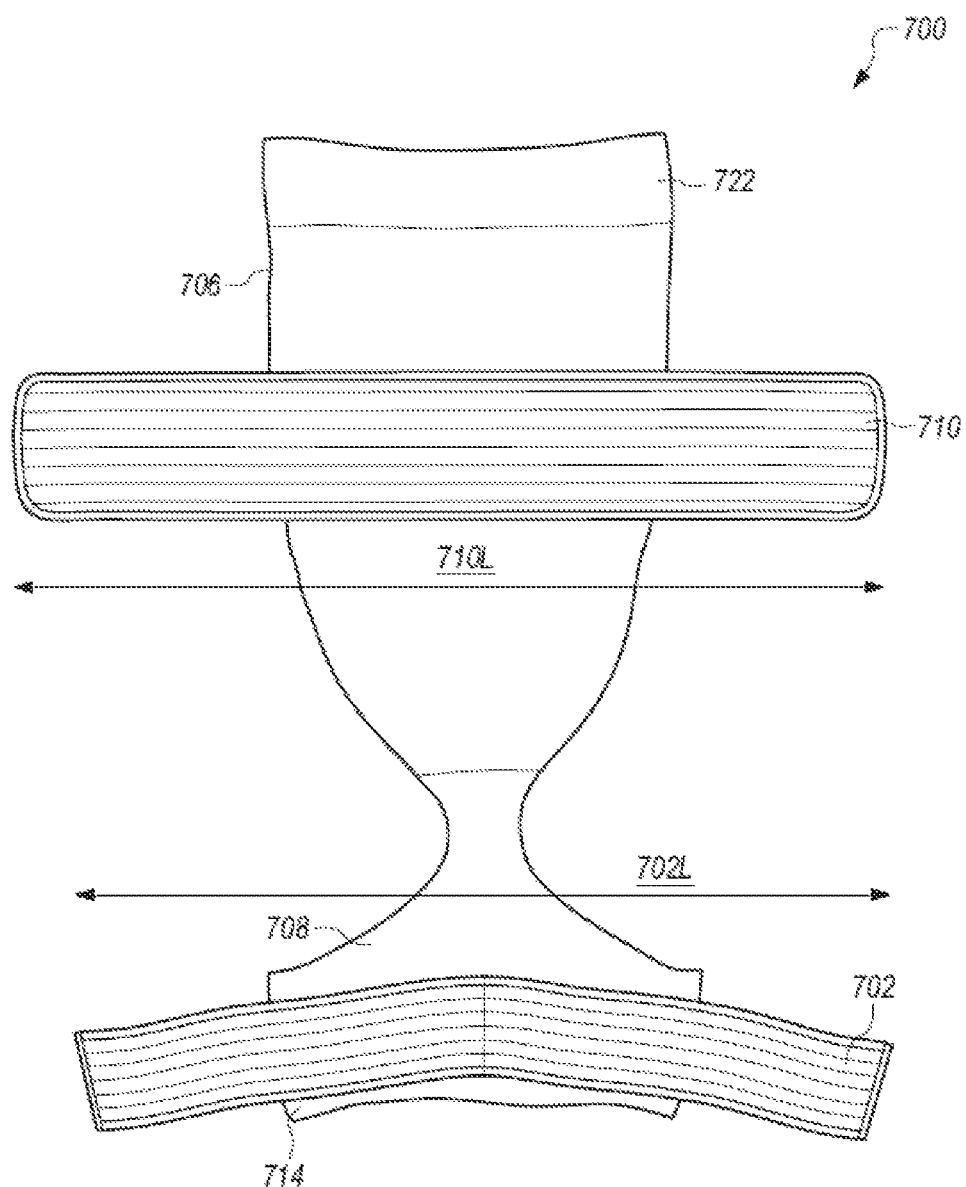
FIG. 7 is a bottom view of an embodiment of the support assembly shown in the undressed configuration.

As used herein, an "undressed configuration" is understood to mean when the assembly body 106 is decoupled from the user 101 and both the first assembly arm 102 and the second assembly arm 210 are detached from the first assembly arm 102. Two non-limiting, non-exclusive examples of the undressed configuration of the support assembly 100 are illustrated in FIGS. 6-7. The support assembly 100 is movable between the dressed configuration, the partially dressed configuration, and the undressed configuration.

The support assembly 100 provides support to various portions of the user 101. For example, the support assembly 100 can support a transverse incision site 420 (for example, illustrated in FIG. 4) of the user 101. In various embodiments, the support assembly 100 can provide greater support to the transverse incision site 420 than the rest of a torso 105 of the user 101 and/or an abdomen 107 of the user 101. As non-exclusive, non-limiting examples, the support assembly 100 can support one or more transverse incision sites 420 utilized in cesarean sections and hysterectomies.

The support assembly 100 offers a number of advantages to the user 101. For example, the support assembly 100 can be configured to allow the user 101 to maintain a full range of hip motion while the support assembly 100 is in the dressed configuration. The support assembly 100 can be configured to allow the user 101 to sit, walk, and use the restroom while the support assembly 100 is in the dressed configuration. In some embodiments, the support assembly 100 can be donned and doffed over a head of the user 101, while the support assembly 100 is in the partially dressed configuration. In other embodiments, the support assembly 100 can be configured to prevent binding around an anterior sacroiliac joint of the user 101 while the support assembly 100 is in the dressed configuration. In various embodiments, the support assembly 100 can be configured to mitigate shear forces on the transverse incision site 420, while the support assembly 100 is in the dressed configuration and the user 101 dons or doffs other clothing.

The support assembly 100 can vary depending on its design requirements. It is understood that the support assembly 100 can include additional components, systems, subsystems, and elements other than those specifically shown and/or described herein. Additionally, or alternatively, the support assembly 100 can omit one or more of the components, systems, subsystems, and elements that are specifically shown and/or described herein. The support assembly 100 can be configured to have increased flexibility and pliability. In the embodiment illustrated in FIG. 1, the support assembly 100 can include the first assembly arm 102, a first arm fastener 104, the assembly body 106, and/or a groin portion 108.

The first assembly arm 102 can provide transverse support to the torso 105 of the user 101. The first assembly arm 102 can be coupled to the assembly body 106. As used herein, "coupled" can be understood to mean, without limitation, one or more of the following: attached (selectively and/or removably), bolted, constrained to, engaged (mutually and/or unilaterally), fixed, integrally formed with, interlocked, locked, mated, mounted (pivotally and/or rotatably), secured, set, joined, linked, welded or otherwise connected. It is appreciated that the coupling can be permanent or temporary.

The first assembly arm 102 can be substantially parallel to the transverse incision site 420 of the user 101 while the first assembly arm 102 is coupled to the assembly body 106, and/or the support assembly 100 is in the dressed configuration. In some embodiments, the first assembly arm 102 can be uncoupled from the assembly body 106. The first assembly arm 102 can be coupled to the assembly body 106 so that there is an increased supportive force applied to the transverse incision site 420 of the user 101. The first assembly arm 102 can be configured to adjust a transverse supportive force to the transverse incision site 420 of the user 101. In other words, the first assembly arm 102 can be selectively adjusted to meet the supportive force requirements of the user 101. For example, the coupling of the first assembly arm 102 to the assembly body 106 can be selectively tightened or loosened.

As used herein, the "transverse supportive force" is understood to mean a substantially transverse vector of supportive force that runs: (i) perpendicular to the torso 105 of the user 101, and (ii) parallel to the transverse incision site 420 of the user 101. The transverse supportive force can be provided by a fabric (e.g., fabric included in the assembly body 106), a reinforcement (e.g., an incision support layer 216, illustrated in FIG. 2), or any other suitable component of the support assembly 100.

The first assembly arm 102 can encircle the user 101. In some embodiments, the first assembly arm 102 can encircle around the user 101 more than once (e.g., the first assembly arm 102 twice encircles around the user 101). The first assembly arm 102 can be adjustable to cover any portion of the user 101. In certain embodiments, the first assembly arm 102 can be configured to contact and/or cover a peri-pelvic area 421 (illustrated in FIG. 4) of the user 101. In the embodiment illustrated in FIG. 1, the first assembly arm 102 partially covers the peri-pelvic area 421 of the user 101. In certain embodiments, the first assembly arm 102 can support the entirety of the transverse incision site 420 of the user 101 when the support assembly 100 is in the dressed configuration. In other embodiments, the first assembly arm 102 can be configured to be adjustable to substantially cover the transverse incision site 420 of user 101 when the support assembly 100 is in the dressed configuration.

The first assembly arm 102 can vary depending on the design requirements of the support assembly 100, the first arm fasteners 104, and/or the assembly body 106. It is understood that the first assembly arm 102 can include additional components, systems, subsystems, and elements other than those specifically shown and/or described herein. Additionally, or alternatively, the first assembly arm 102 can omit one or more of the components, systems, subsystems, and elements that are specifically shown and/or described herein.

The first assembly arm 102 can be formed from any suitable material. In some embodiments, the first assembly arm 102 can be at least partially formed from a fabric, a textile, a plastic, a natural material, a synthetic material, a resilient material, and/or a rubber. The first assembly arm 102 can include the first arm fastener 104. In some embodiments, the first assembly arm 102 can be coupled to the groin portion 108. In various embodiments, in the dressed configuration, the first assembly arm 102 can overlap the assembly body 106 so that both the first assembly arm 102 and the assembly body 106 cover at least some of the transverse incision site 420 of the user 101. In various embodiments, in the dressed configuration, only the first assembly arm 102 covers the transverse incision site 420 of the user 101.

The first arm fastener 104 fastens the first assembly arm 102 to the assembly body 106. The first arm fastener 104 can be configured to adjust the supportive force provided by the first assembly arm 102. For example, the first arm fastener 104 can fasten the first assembly arm 102 to the assembly body 106 so that the support assembly 100 provides lesser support to the transverse incision site 420. As used herein, "fastened" can be understood to mean, without limitation, one or more of the following: fastened (selectively and/or removably), secured, locked, interlocked, clamped, fixed, immobilized, latched, or otherwise fastened. It is appreciated that the fastening can be permanent or temporary (e.g., detachably fastened).

In certain embodiments, the support assembly 100 provides a greater supportive force to the transverse incision site 420 than the rest of the torso 105 of the user 101. The first arm fastener 104 can enable the first assembly arm 102 to be movable between a fastened configuration (two non-limiting, non-exclusive examples are illustrated in FIGS. 1-2) and an unfastened configuration (five non-limiting, non-exclusive examples are shown in FIGS. 3-7). The first arm fastener 104 can allow the first assembly arm 102 to fasten to itself.

The first arm fastener 104 can vary depending on the design requirements of the support assembly 100, the first assembly arm 102, and/or the assembly body 106. The location and number of first arm fasteners 104 on the first assembly arm 102 can vary. In the embodiment illustrated in FIG. 1, the first arm fastener 104 can be positioned to couple the first assembly arm 102 to the assembly body 106 near the hips of the user 101. In certain embodiments, the support assembly 100 can include a plurality of first arm fasteners 104.

The first arm fastener 104 can be formed from any suitable material. In some embodiments, the first arm fastener 104 can be at least partially formed from a fabric, a textile, a plastic, a natural material, a synthetic material, and/or a rubber. The first arm fastener 104 can include a hook and loop fastener, an adhesive, and/or any suitable fastener known in the art.

The assembly body 106 forms the body of the support assembly 100. The assembly body 106 can be positioned on the user 101 (e.g., in the partially dressed configuration) before moving the support assembly 100 to the dressed configuration. The assembly body 106 can provide an additional transverse supportive force to a portion of the user 101. The assembly body 106 can encircle the torso 105 and/or the abdomen 107 of the user 101. In other embodiments, the assembly body 106 can cover at least a portion of the torso 105 and/or abdomen 107 of the user 101.

The assembly body 106 can be coupled or fastened to the first assembly arm 102. The assembly body 106 can be configured to provide lesser support to the torso 105 and/or the abdomen 107 of the user 101 than the first assembly arm 102 provides to the transverse incision site 420 of the user 101. The assembly body 106 can be configured to be adjustable to meet the supportive force requirements of the user 101.

The assembly body 106 can vary depending on the design requirements of the support assembly 100, the first assembly arm 102, and/or the assembly arm fasteners 104. It is understood that the assembly body 106 can include additional components, systems, subsystems, and elements other than those specifically shown and/or described herein. Additionally, or alternatively, the assembly body 106 can omit one or more of the components, systems, subsystems, and elements that are specifically shown and/or described herein.

The assembly body 106 can be formed from any suitable material. In some embodiments, the assembly body 106 can be at least partially formed from a fabric, a textile, a plastic, a natural material, a synthetic material, a resilient material, and/or a rubber. The assembly body 106 can include the groin portion 108 and a pelvic support layer 214 (for example, illustrated in FIG. 2).

The groin portion 108 covers a groin region 109 of the user 101. The groin portion 108 can be coupled to the first assembly arm 102, the assembly body 106, and/or any suitable portion of the support assembly 100. The groin portion 108 can allow the user 101 to don and doff additional clothing while the support assembly 100 is in the dressed configuration. In other embodiments, the groin portion 108 can allow the user 101 to use the restroom while the support assembly 100 is in the partially dressed configuration. For example, the first assembly arm 102 can be moved to the unfastened configuration, and the support assembly 100 can be moved to the undressed configuration so that the groin portion 108 can be removed from an underside of the user 101. In the fastened configuration, the first assembly arm 102 can secure the positioning of the groin portion 108. The groin portion 108 can be removed from the underside of the user 101 while the first assembly arm 102 remains in the fastened configuration. The groin portion 108 can allow the user 101 to receive wound care while the support assembly 100 is in the partially dressed configuration. The groin portion 108 can be continuously formed with the assembly body 106.

The groin portion 108 can vary depending on the design requirements of the support assembly 100, the first assembly arm 102, the assembly arm fasteners 104, and/or the assembly body 106. In some embodiments, the groin portion 108 can include a drop-front panel. The groin portion 108 can be formed from any suitable material. In some embodiments, the groin portion 108 can be at least partially formed from a fabric, a textile, a plastic, a natural material, a synthetic material, and/or a rubber.

FIG. 2 is a simplified cross-sectional view of the user 101 and an embodiment of the support assembly 100 taken on line 2-2 in FIG. 1. In the embodiment illustrated in FIG. 2, the support assembly 100 is illustrated in the dressed configuration, and the first assembly arm 102 is in the fastened configuration.

As shown in FIG. 2, the user 101 is substantially surrounded and/or encircled by the assembly body 106. In various embodiments, the first assembly arm 102 can be coupled to a second assembly arm 210 located at the rear of the user 101. In certain embodiments, the second assembly arm 210 can be coupled to the first assembly arm 102 and/or the assembly body 106. In other embodiments, the second assembly arm 210 can be substantially similar to the first assembly arm 102. The second assembly arm 210 can wrap around the entirety of the torso 105 (illustrated in FIG. 1) of the user 101 or just a portion of the torso 105 of the user 101. In various embodiments, the second assembly arm 210 can wrap around the torso 105 of the user 101 more than once. The second assembly arm 210 can be adjustable to cover any portion of the user 101. The second assembly arm 210 can be selectively fastenable to the first assembly arm 102, as described herein.

The second assembly arm 210 can vary depending on the design requirements of the support assembly 100, the first assembly arm 102, the first arm fasteners 104, and/or the assembly body 106. It is understood that the second assembly arm 210 can include additional components, systems, subsystems, and elements other than those specifically shown and/or described herein. Additionally, or alternatively, the second assembly arm 210 can omit one or more of the components, systems, subsystems, and elements that are specifically shown and/or described herein.

The second assembly arm 210 can be formed from any suitable material. In some embodiments, the second assembly arm 210 can be at least partially formed from a fabric, a textile, a plastic, a natural material, a synthetic material, a resilient material, and/or a rubber. The second assembly arm 210 can be configured to be fastened by the first arm fastener 104. For example, the second assembly arm 210 can include loops to receive hooks formed on the first arm fastener 104. In some embodiments, the second assembly arm 210 can be coupled and/or secured to the assembly body 106 via a second arm securer 212. As displayed in FIG. 2, the second arm securer 212 can include a securing layer positioned between the second assembly arm 210 and the assembly body 106. In various embodiments, in the dressed configuration, the first assembly arm 102 is fastened to the second assembly arm 210 at one or more fastening points 418 (for example, as illustrated in FIG. 4).

A pelvic support layer 214 can be coupled to the first assembly arm 102, as shown in FIG. 2. The pelvic support layer 214 provides additional support to a pelvic region of the user 101. The pelvic support layer 214 can be positioned around a portion of the pelvic region of the user 101. The pelvic support layer 214 can be configured to provide a transverse supportive force to the transverse incision site 420 (illustrated in FIG. 4) of the user 101. The pelvic support layer 214 can be adjustable to meet the supportive force requirements of the user 101. The pelvic support layer 214 can be coupled to the groin portion 108 (illustrated in FIG. 1).

The pelvic support layer 214 can vary depending on the design requirements of the support assembly 100, the first assembly arm 102, the assembly body 106, and/or the groin portion 108. The pelvic support layer 214 can be formed from any suitable material. In some embodiments, the pelvic support layer 214 can be at least partially formed from a fabric, a textile, a plastic, a natural material, a synthetic material, a resilient material, and/or a rubber. In certain embodiments, the pelvic support layer 214 can be coupled to an incision support layer 216. In other embodiments, the pelvic support layer 214 can include the incision support layer 216.

The incision support layer 216 can provide additional support and/or padding for the transverse incision site 420. The incision support layer 216 can vary depending on the design requirements of the support assembly 100, the first assembly arm 102, the assembly body 106, and/or the pelvic support layer 214. The incision support layer 216 can be formed from any suitable material. In some embodiments, the incision support layer 216 can be at least partially formed from a fabric, a textile, a plastic, a natural material, a synthetic material, a resilient material, and/or a rubber. In the dressed configuration, the incision support layer 216 can be positioned between the pelvic support layer 214 and the assembly body 106. In other embodiments, in any configuration, the pelvic support layer 214 can be positioned between the incision support layer 216 and the first assembly arm 102.

FIG. 3 is a front view of the user 301 and an embodiment of the support assembly 300 shown in the partially dressed configuration. In the embodiment illustrated in FIG. 3, the support assembly 300 includes the first assembly arm 302 and the first arm fastener 304. In this embodiment, the first assembly arm 302 can encircle the torso 105 (illustrated in FIG. 1) and/or the abdomen 107 (illustrated in FIG. 1) of the user 301, near the hips of the user 301. In FIG. 3, the first assembly arm 302 is displayed in the unfastened configuration.

The first arm fastener 304 can be used to fasten the first assembly arm 302 to itself. As a non-limiting, non-exclusive example, the first arm fastener 304 can include hooks, and the first assembly arm 302 can be formed with loops that receive the hooks. The assembly body 306 can encircle and/or cover the torso 105 and/or the abdomen 107 of the user 301 before moving the first assembly arm 302 to the fastened configuration. The first assembly arm 302 can encircle and/or cover the torso 105 and/or the abdomen 107 of the user 301 so that the first assembly arm 302 is in contact with the assembly body 306 and/or the groin portion 308. In the embodiment illustrated in FIG. 3, the first assembly arm 302 is in contact with both the assembly body 306 and the groin portion 308.

FIG. 4 is a left side view of the user 401 and an embodiment of the support assembly 400. In the embodiment illustrated in FIG. 4, the support assembly 400 includes the first assembly arm 402, the first arm fastener 404, and a fastening point 418. In this embodiment, the first assembly arm 402 is shown in an unfastened configuration, and the first assembly arm 402 is positioned away from the transverse incision site 420 of the user 401. In this embodiment, in the unfastened configuration and the partially dressed configuration, the assembly arm 402 can hang toward a lower portion of the user 401. The groin portion 408 can be coupled to both the first assembly arm 402 and the assembly body 406, so that the groin portion 408 is positioned between the first assembly arm 402 and the assembly body 406. The first assembly arm 402 can include a first arm end 403 that is fastenable to the first assembly arm 402, the assembly body 406, and/or the second assembly arm 210 (illustrated in FIG. 2).

The first arm end 403 can include the first arm fastener 404 that fastens the first arm end 403 to the first assembly arm 402, the assembly body 406, the second assembly arm 210, and/or the fastening point 418. In some embodiments, the first arm fastener 404 can be positioned away from the first arm end 403 so that the first arm fastener 404 is not located on the first arm end 403. The first arm end 403 can be pulled underneath the groin region 109 (illustrated in FIG. 1) of the user 401 in order to fasten the first arm fastener 404 to the fastening point 418.

The fastening point 418 can be fastened by the first arm fastener 404. For example, the fastening point 418 can be formed with loops to receive the hooks of the first arm fastener 404. In some embodiments, the fastening point 418 can be coupled to the assembly body 406. In other embodiments, the fastening point 418 can be integrally formed with the assembly body 406 or any suitable component of the support assembly 400.

The fastening point 418 can vary depending on the design requirements of the support assembly 400, the first assembly arm 402, the first arm end 403, and/or the assembly body 406. In some embodiments, the fastening point 418 can be at least partially formed from a fabric, a textile, a plastic, a natural material, a synthetic material, and/or a rubber. The positioning and number of fastening points 418 can vary. One non-limiting, non-exclusive example of a demonstrative location of the fastening point 418 is illustrated in FIG. 4 (e.g., on the assembly body 406, near a hip of the user 401). The first assembly arm 402 and the second assembly arm 210 can be integrally formed with one or more fastening points 418. The fastening point 418 can be any suitable fastening point known in the art.

The transverse incision site 420 can represent any wound site, such as those non-exclusive, non-limiting examples provided herein. The support assembly 400 can be configured to provide support to the transverse incision site 420. The first assembly arm 402 and/or the assembly body 406 can engage the transverse incision site 420 in order to provide support to the transverse incision site 420. The transverse incision site 420 can be located in the peri-pelvic area 421 of the user 401.

FIG. 5 is a left side view of the user 501 and an embodiment of the support assembly 500 shown in the partially dressed configuration. In the embodiment illustrated in FIG. 5, the support assembly 500 includes the first assembly arm 502, the first arm fastener 504, the assembly body 506, and the second assembly arm 510. In this embodiment, both the first assembly arm 502 and the second assembly arm 510 are shown in the unfastened configuration. In the unfastened configuration, both the first assembly arm 502 and the second assembly arm 510 can be positioned toward the lower portion of the user 501 when the assembly body 506 encircles the user 501.

In some embodiments, to move to the dressed configuration from the undressed configuration, the first assembly arm 502 is positioned over the transverse incision site 520, and the first arm fastener 504 is fastened to the second assembly arm 510. The second assembly arm 510 can be positioned around the user 501 so that the first assembly arm 502 can be fastened to the second assembly arm 510. The first assembly arm 502 and the groin portion 508 can wrap between the legs 311 (illustrated in FIG. 3) of the user 501, so that the groin region 109 (illustrated in FIG. 1) of the user 501 is covered by the groin portion 508.

FIG. 6 is a top view of an embodiment of the support assembly 600 shown in the undressed configuration. In the embodiment illustrated in FIG. 6, the support assembly 600 includes the first assembly arm 602, the assembly body 606, and the second assembly arm 610. In this embodiment, the first assembly arm 602 and the second assembly arm 610 are illustrated in the unfastened configuration. In the undressed configuration, at least a portion of the assembly body 606 can have a somewhat hourglass-shaped configuration. The interior portions of some of the components of the support assembly 600 are illustrated in FIG. 6.

In the embodiment shown in FIG. 6, the first assembly arm 602 includes two first arm fasteners 604 located on opposing first arm ends 403 (illustrated in FIG. 4) of the first assembly arm 602. The first assembly arm 602 can be coupled to the pelvic support layer 614 near a center of the first assembly arm 602. The first assembly arm 602 and the pelvic support layer 614 can be positioned simultaneously or separately. The first assembly arm 602, the second assembly arm 610, and the pelvic support layer 614 can be substantially parallel while the support assembly 600 is in the undressed configuration and the first assembly arm 602 and the second assembly arm 610 are in the unfastened configuration.

In some embodiments, an incision support layer 616 can be coupled to both the pelvic support layer 614 and the groin portion 608 so that at least a portion of an interior of the groin portion 608 is covered by the incision support layer 616 (e.g., as illustrated in FIG. 6). The groin portion 608 can be adjacent to the pelvic support layer 614.

In certain embodiments, the components of the support assembly 600 can be stitched together. For example, as shown in FIG. 6, the first assembly arm 602 is stitched to the pelvic support layer 614. The pelvic support layer 614 can be stitched to the groin portion 608. The incision support layer 616 can be stitched to the pelvic support layer 614 and the groin portion 608. The groin portion 608 can be stitched to the assembly body 606. A second arm securer 612 can be stitched to the assembly body 606. The second assembly arm 610 can be stitched to the second arm securer 612 so that the second arm securer 612 is positioned between the assembly body 606 and the second assembly arm 610.

An edge band 622 can be stitched and/or coupled to the assembly body 606. The edge band 622 can be configured to conform to a waist or any suitable portion of the user 101. The edge band 622 can vary depending on the design requirements of the support assembly 600 and the assembly body 606. The edge band 622 can be at least partially formed from a flexible material, a resilient material, and/or a malleable material.

As illustrated in the embodiment in FIG. 6, the first assembly arm 602 can have a first arm length 602L and the second assembly arm 610 can have a second arm length 610L. The first arm length 602L and the second arm length 610L are adjustable in length to meet the individual supportive force requirements of the user 101. The first arm length 602L and the second arm length 610L can be separately adjustable. The first arm fasteners 604 can be coupled to the first assembly arm 602 along the entirety of the first arm length 602L. In other embodiments, the first arm fasteners 604 can be coupled to the second assembly arm 610 along the entirety of the second arm length 610L.

FIG. 7 is a bottom view of an embodiment of the support assembly 700 shown in the undressed configuration. In the embodiment illustrated in FIG. 7, the support assembly 700 includes the first assembly arm 702, the assembly body 706, and the second assembly arm 710. The first assembly arm 702 has the first arm length 702L and the second assembly arm 710 has the second arm length 710L. In this embodiment, the support assembly 700 is shown in an undressed configuration. In this embodiment, the first assembly arm 702 and the second assembly arm 710 are in the unfastened configuration. The exterior-facing portions of the support assembly 700 are illustrated in FIG. 7, including the groin portion 708, the pelvic support layer 714, and the edge band 722.

Figure 8:
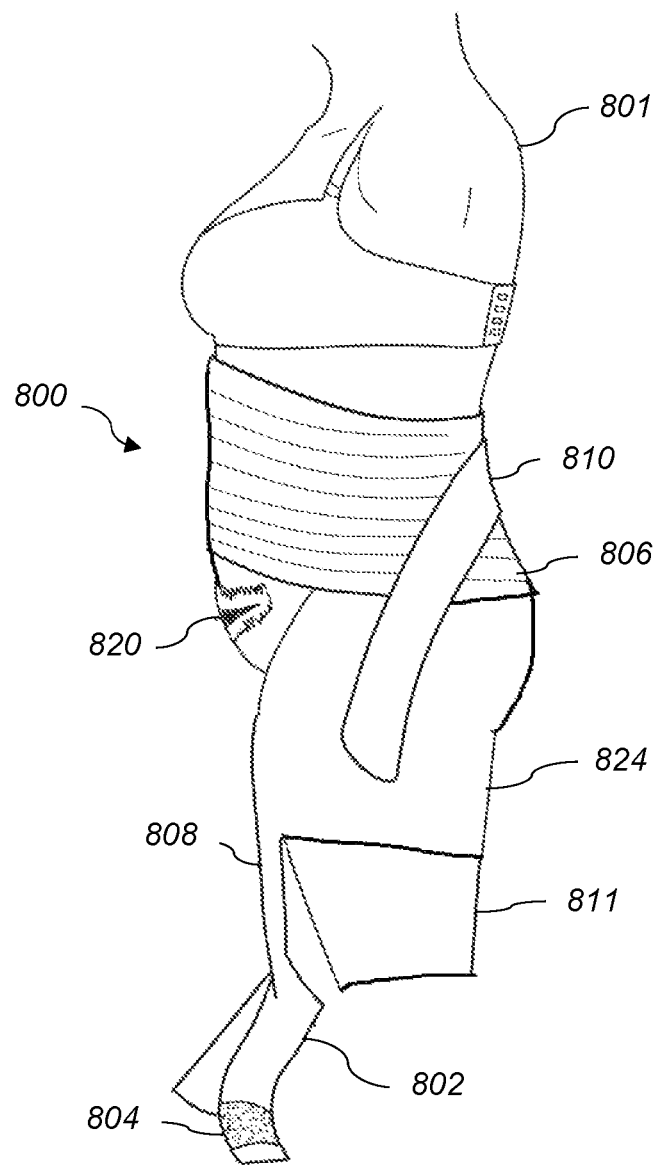
FIG. 8 is a left side view of the user and yet another embodiment of support assembly shown in the partially dressed configuration.

FIG. 8 is a left side view of the user 801 and yet another embodiment of support assembly 800 shown in the partially dressed configuration. In the embodiment illustrated in FIG. 8, the support assembly 800 includes the first assembly arm 802, the first arm fastener 804, the assembly body 806, and the second assembly arm 810. In this embodiment, both the first assembly arm 802 and the second assembly arm 810 are shown in the unfastened configuration. In the unfastened configuration, both the first assembly arm 802 and the second assembly arm 810 can be positioned posteriorly and/or anteriorly toward the lower portion of the user 801 when the assembly body 806 encircles the user 801.

In certain embodiments, the support body 806 can include a leg portion 824. The leg portion 824 can be configured to encircle at least one of the legs 811 of the user 801. The leg portion 824 can vary to fit the design requirements of the support body 800. For example, the leg portion 824 can be lengthened or shortened to meet specific inseam measurements. In non-limiting, non-exclusive embodiments, the leg portion 824 can be lengthened or shortened so that the support assembly 800 is somewhat similar to athletic shorts, running shorts, walking shorts, hiking shorts, cycling shorts, swim/board shorts, golf shorts, bikini panty, boy short panty, briefs, boxers, boxer briefs, jockstraps, bikini bottoms, thongs, tights, and/or pantaloons. It is appreciated, that in some embodiments, the leg portion 824 can be short enough to avoid contact with the legs 811, and may only be in contact with the peri-pelvic area 421 (illustrated in FIG. 4) of the user 801 and/or the hips of the user 801.

In various embodiments, the leg portion 824 can be integrally formed with at least one of the first assembly arm 802, the support body 806, the groin portion 808, and/or the second assembly arm 810. In other embodiments, the leg portion 824 can be separately formed and coupled to at least one of the first assembly arm 802, the support body 806, the groin portion 808, and/or the second assembly arm 810.

In some embodiments, to move to the dressed configuration from the undressed configuration, the first assembly arm 802 is positioned over the transverse incision site 820, and the first arm fastener 804 is fastened to the second assembly arm 810. The second assembly arm 810 can be positioned around the user 801 so that the first assembly arm 802 can be fastened to the second assembly arm 810. The first assembly arm 802 and the groin portion 808 can extend from the groin region 109 (illustrated in FIG. 1) of the user 801 to at least the peri-pelvic area 421 (illustrated in FIG. 4). In some embodiments, the first assembly arm 801 can be configured to extend up to the abdomen 107 (illustrated in FIG. 1) of the user 801 and/or an upper portion of the torso 105 (illustrated in FIG. 1) of the user 801.

In various embodiments, such as shown in FIG. 8, the first assembly arm 802 and/or the groin portion 808 can extend and/or hang anteriorly from the user 801. In certain embodiments, the first assembly arm 802 and/or the groin portion 808 can be coupled to an anterior side of the leg portion 824. FIG. 8 contrasts the embodiment shown in FIG. 5, where the first assembly arm 502 and/or the groin portion 508 hang anteriorly from the user 501.

Figure 9:
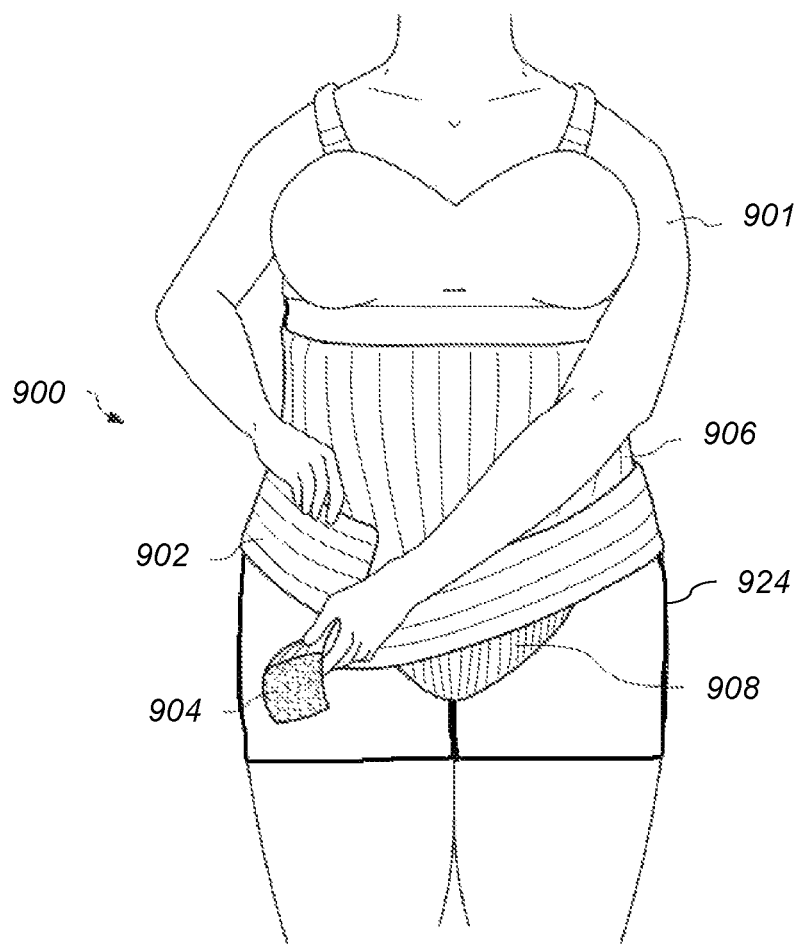
FIG. 9 is a front view of the user and yet another embodiment of the support assembly shown in a partially dressed configuration.

FIG. 9 is a front view of the user 901 and yet another embodiment of the support assembly 900, shown in a partially dressed configuration. In the embodiment illustrated in FIG. 9, the support assembly 900 includes the first assembly arm 902, the first arm fastener 904, the assembly body 906, the groin portion 908, and the leg portion 924. In this embodiment, the first assembly arm 902 can encircle the torso 105 (illustrated in FIG. 1) and/or the abdomen 907 (illustrated in FIG. 1) of the user 901, near the hips of the user 901. In FIG. 9, the first assembly arm 902 is displayed in the unfastened configuration. In the fastened configuration, the first assembly 902 can be in contact with itself, the support body 906, the groin region 908, and/or the leg portion 924.

The first arm fastener 904 can be used to fasten the first assembly arm 902 to itself. As a non-limiting, non-exclusive example, the first arm fastener 904 can include hooks, and the first assembly arm 902 can be formed with loops that receive the hooks. The assembly body 906 can encircle and/or cover the torso 105 and/or the abdomen 107 of the user 901 before moving the first assembly arm 902 to the fastened configuration. The first assembly arm 902 can encircle and/or cover the torso 105 and/or the abdomen 107 of the user 901 so that the first assembly arm 902 is in contact with the assembly body 906 and/or the groin portion 908.

It is appreciated that the embodiments of the support assembly 900 illustrated in FIGS. 8 and 9 can accommodate many body types of various users 901. The support assembly 900 can be configured to provide support for any suitable peri-pelvic procedure, including, but not limited to, orthopedic reconstructions, gastroenterology, gastrointestinal, vascular, open, and laparoscopic procedures. The support assembly 900 can also be modified to provide support to regions outside the peri-pelvic area 421 (illustrated in FIG. 4), such as areas within the torso 105 and/or the abdomen 107.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications can be made while remaining within the spirit and scope herein.

It is understood that although a number of different embodiments of the peri-pelvic post-operative support assembly have been illustrated and described herein, one or more features of any one embodiment can be combined with one or more features of one or more of the other embodiments, provided that such combination satisfies the intent of the present invention.

While a number of exemplary aspects and embodiments of the peri-pelvic post-operative support assembly have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope, and no limitations are intended to the details of construction or design herein shown.

What is claimed is:

1. A support assembly for supporting a transverse incision site at a peri-pelvic area of a user, the user having an abdomen, at least one leg, and a groin region, the support assembly comprising:
   an assembly body that is configured to encircle (i) the abdomen of the user, and (ii) the at least one leg of the user, the assembly body including a pelvic support layer that is configured to provide a transverse supportive force to the transverse incision site of the user; and
   a first assembly arm that is coupled to the pelvic support layer, the first assembly arm extending anteriorly from the assembly body, the first assembly arm being configured to extend from the groin region of the user and secure to the assembly body to adjust the transverse supportive force to the transverse incision site at the peri-pelvic area, the first assembly arm being movable so that the transverse incision site at the peri-pelvic area is uncovered by the assembly body and the first assembly arm.

2. The support assembly of claim 1 further comprising a second assembly arm that is secured to the assembly body, wherein the first assembly arm has a first arm end that is detachably fastenable to one of (i) the second assembly arm, and (ii) the assembly body.

3. The support assembly of claim 2 wherein the first arm end includes a first arm fastener that detachably fastens the first assembly arm to one of (i) the second assembly arm, and (ii) the assembly body.

4. The support assembly of claim 1 wherein the assembly body includes a groin portion configured to cover the groin region of the user, the groin portion being positioned adjacent to the pelvic support layer.

5. The support assembly of claim 1 wherein the assembly body includes an edge band that encircles and is configured to conform to a portion of the abdomen of the user, the edge band being at least partially formed from an elastic material.

6. The support assembly of claim 1 further comprising a second assembly arm that is secured to the assembly body, the assembly body including a second arm securer, wherein the second assembly arm is coupled to the second arm securer of the assembly body.

7. The support assembly of claim 1 further comprising a second assembly arm that is secured to the assembly body, wherein the support assembly is movable between (i) a dressed configuration wherein the assembly body encircles the user and the second assembly arm is fastened to the first assembly arm, (ii) a partially dressed configuration wherein the assembly body encircles the user and the second assembly arm is detached from the first assembly arm, and (iii) an undressed configuration wherein the assembly body is decoupled from the user and the second assembly arm is detached from the first assembly arm.

8. The support assembly of claim 7 wherein in the dressed configuration, the pelvic support layer is positioned in between the first assembly arm and an incision support layer.

9. The support assembly of claim 7 wherein, in the dressed configuration, the first assembly arm is fastened to the second assembly arm at a plurality of fastening points.

10. The support assembly of claim 7 wherein the support assembly is movable between the dressed configuration and the partially dressed configuration without removing the assembly body from the abdomen of the user.

11. The support assembly of claim 7 wherein in the undressed configuration, the first assembly arm, the second assembly arm, and the pelvic support layer are substantially parallel to one another.

12. A support assembly for supporting a transverse incision site at a peri-pelvic area of a user, the user having an abdomen, at least one leg, and a groin region, the support assembly comprising:
   an assembly body that is configured to encircle (i) the abdomen of the user, and (ii) the at least one leg of the user, the assembly body including a pelvic support layer that is configured to provide a transverse supportive force to the transverse incision site of the user; and
   a first assembly arm that is coupled to the pelvic support layer, the first assembly arm extending anteriorly from the assembly body, the first assembly arm being configured to extend from the groin region of the user and secure to one of the first assembly arm and the assembly body to adjust the transverse supportive force to the transverse incision site at the peri-pelvic area;
   wherein the support assembly is movable between (i) a dressed configuration wherein the assembly body encircles the user, and the first assembly arm is fastened to one of the first assembly arm and the assembly body, (ii) a partially dressed configuration wherein the assembly body encircles the user, and the first assembly arm is detached from one of the first assembly arm and the assembly body, the transverse incision site at the peri-pelvic area being uncovered by the assembly body and the first assembly arm in the partially dressed configuration, and (iii) an undressed configuration wherein the assembly body is decoupled from the user, and the first assembly arm is detached from one of the first assembly arm and the assembly body.

13. The support assembly of claim 12 wherein the assembly body includes a groin portion that is configured to cover the groin region of the user, the groin portion being positioned adjacent to the pelvic support layer.

14. The support assembly of claim 12 wherein the assembly body includes an edge band that encircles and is configured to conform to a portion of the abdomen of the user, the edge band being at least partially formed from an elastic material.

15. The support assembly of claim 12 wherein, in the dressed configuration, the pelvic support layer is positioned in between the first assembly arm and an incision support layer.

16. The support assembly of claim 12 wherein, in the undressed configuration, at least a portion of the assembly body has a somewhat hourglass-shaped configuration.

17. The support assembly of claim 12 further comprising a second assembly arm that is coupled to a second arm securer of the assembly body, the second assembly arm being detachably fastenable to the first assembly arm, the second arm securer being coupled to the assembly body.

18. The support assembly of claim 12 wherein the first assembly arm has a first arm end that is detachably fastenable to the assembly body.

19. The support assembly of claim 18 wherein the first arm end includes a first arm fastener that detachably fastens the first assembly arm to at least one of the assembly body and the first assembly arm.

20. A support assembly for supporting a transverse incision site at a peri-pelvic area of a user, the user having an abdomen, at least one leg, and a groin region, the support assembly comprising:
- an assembly body that is configured to encircle (i) the abdomen of the user, and (ii) the at least one leg of the user;
- a first assembly arm that extends anteriorly from the assembly body, the first assembly arm being configured to extend from the groin region of the user and secure to the assembly body to adjust a transverse supportive force to the transverse incision site at the peri-pelvic area;
- a pelvic support layer that is coupled to the first assembly arm, the pelvic support layer being simultaneously positionable with the first assembly arm; and
- a second assembly arm that is secured to the assembly body, the assembly body including a second arm securer, wherein the second assembly arm is coupled to the second arm securer of the assembly body;
- wherein the support assembly is movable between (i) a dressed configuration wherein the assembly body encircles the user and the second assembly arm is fastened to the first assembly arm, and the pelvic support layer is positioned in between the first assembly arm and an incision support layer, (ii) a partially dressed configuration wherein the assembly body encircles the user and the second assembly arm is detached from the first assembly arm, and the pelvic support layer is positioned away from the transverse incision site of the user, and (iii) an undressed configuration wherein the assembly body is decoupled from the user and the second assembly arm is detached from the first assembly arm.

* * * * *